US012778540B2

(12) United States Patent
Swan et al.

(10) Patent No.: US 12,778,540 B2
(45) **Date of Patent: *Nov. 3, 2026**

(54) ULTRASOUND IMAGING SYSTEM WITH AUTOMATIC IMAGE SAVING

(71) Applicant: FUJIFILM SONOSITE, INC., Bothewll, WA (US)

(72) Inventors: Wendy Swan, Lake Forest Park, WA (US); Daniel Shelton, Prosper, TX (US); Somnath Banik, Bothell, WA (US)

(73) Assignee: FUJIFILM SONOSITE, INC., Bothell, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/937,455

(22) Filed: Nov. 5, 2024

(65) Prior Publication Data

US 2025/0057502 A1 Feb. 20, 2025

Related U.S. Application Data

(60) Division of application No. 18/054,170, filed on Nov. 10, 2022, now Pat. No. 12,178,639, which is a (Continued)

(51) Int. Cl.
*A61B 8/00* (2006.01)
*A61B 8/08* (2006.01)
(Continued)

(52) U.S. Cl.
CPC ............ *A61B 8/0841* (2013.01); *A61B 8/463* (2013.01); *A61B 8/5276* (2013.01); (Continued)

(58) Field of Classification Search
None
See application file for complete search history.

(56) References Cited

U.S. PATENT DOCUMENTS

| | | | |
|---|---|---|---|
| 6,217,515 | B1 | 4/2001 | Yamakawa et al. |
| 10,675,004 | B2 | 6/2020 | Lundberg et al. |

(Continued)

FOREIGN PATENT DOCUMENTS

| | | | |
|---|---|---|---|
| EP | 0984298 | A2 | 3/2000 |
| JP | 2012-213606 | A | 11/2012 |

(Continued)

OTHER PUBLICATIONS

Decision to Grant received for Japanese Patent Application No. 2020-570697, mailed on Jan. 9, 2024, 5 pages (2 pages of English Translation and 3 pages of Original Document).

(Continued)

*Primary Examiner* — Amal Aly Farag
(74) *Attorney, Agent, or Firm* — Womble Bond Dickinson (US) LLP

(57) ABSTRACT

Ultrasound imaging systems for automatically identifying and saving ultrasound images relevant to a needle injection procedure, and associated systems and methods, are described herein. For example, an ultrasound imaging system includes a transducer for transmitting/receiving ultrasound signals during a needle injection procedure, and receive circuitry configured to convert the received ultrasound signals into ultrasound image data. The image data can be stored in a buffer memory. A processor can analyze the image data stored in the buffer memory to identify image data that depicts a specified injection event of the needle injection procedure, and the identified image data can be stored in a memory for archival purposes.

20 Claims, 3 Drawing Sheets

Related U.S. Application Data continuation of application No. 16/012,627, filed on Jun. 19, 2018, now Pat. No. 11,529,116.

(51) Int. Cl.

| | |
|---|---|
| ***G01S 7/52*** | (2006.01) |
| ***G01S 15/89*** | (2006.01) |
| ***G06N 20/00*** | (2019.01) |
| ***G06T 7/00*** | (2017.01) |
| ***G06T 7/20*** | (2017.01) |
| ***G16H 30/20*** | (2018.01) |

(52) U.S. Cl.

CPC ........ *G01S 7/5202* (2013.01); *G01S 7/52053* (2013.01); *G01S 7/52085* (2013.01); *G01S 15/8911* (2013.01); *G06N 20/00* (2019.01); *G16H 30/20* (2018.01); *A61B 2560/0475* (2013.01); *G06T 7/0016* (2013.01); *G06T 7/20* (2013.01); *G06T 2207/10132* (2013.01); *G06T 2207/20081* (2013.01)

(56) References Cited

U.S. PATENT DOCUMENTS

| | | | |
|---|---|---|---|
| 2012/0078103 | A1 | 3/2012 | Tashiro et al. |
| 2012/0197132 | A1 | 8/2012 | O'Connor |
| 2012/0259237 | A1 | 10/2012 | Axelrod |
| 2013/0274608 | A1 | 10/2013 | Takeda et al. |
| 2014/0243657 | A1 | 8/2014 | Maizes |
| 2016/0173770 | A1 | 6/2016 | Fosodeder et al. |
| 2016/0210511 | A1 | 7/2016 | Leong et al. |
| 2016/0343134 | A1 | 11/2016 | Averkiou et al. |
| 2017/0196535 | A1 | 7/2017 | Arai et al. |
| 2017/0340307 | A1 | 11/2017 | Kano |
| 2018/0021022 | A1 | 1/2018 | Lundberg et al. |
| 2023/0380797 | A1 | 11/2023 | Okamura et al. |

FOREIGN PATENT DOCUMENTS

| | | | |
|---|---|---|---|
| JP | 2013-523343 | A | 6/2013 |
| JP | 2013-192627 | A | 9/2013 |
| JP | 2015-134132 | A | 7/2015 |
| JP | 2016-508797 | A | 3/2016 |
| JP | 2017-209324 | A | 11/2017 |
| WO | 2010/038172 | A1 | 4/2010 |

OTHER PUBLICATIONS

European Search Report and Search Opinion received for European Application No. 19822886.8, mailed on Feb. 25, 2022, 8 pages.

International Preliminary Report on Patentability received for PCT Patent Application No. PCT/US2019/37816, mailed on Dec. 30, 2020, 9 pages.

International Search Report and Written Opinion received for PCT Patent Application No. PCT/US2019/37816, mailed on Sep. 27, 2019, 10 pages.

Non-Final Office Action received for U.S. Appl. No. 18/054,170, mailed on Apr. 22, 2024, 19 pages.

Notice of Allowance received for U.S. Appl. No. 18/054,170, mailed on Sep. 3, 2024, 8 pages.

Notice of Reasons for Refusal received for Japanese Patent Application No. 2024-017775, mailed on Nov. 28, 2024, 6 pages (3 pages of English Translation and 3 pages of Original Document).

Office Action received for Japanese Patent Application No. 2020-570697, mailed on Aug. 3, 2023, 9 pages (5 pages of English Translation and 4 pages of Original Document).

Office Action received for Japanese Patent Application No. 2020-570697, mailed on Dec. 26, 2022, 10 pages (5 pages of English Translation and 5 pages of Original Document).

Office Action received for Japanese Patent Application No. 2020-570697, mailed on Nov. 6, 2023, 4 pages (2 pages of English Translation and 2 pages of Original Document).

Requirement for Restriction/Election received for U.S. Appl. No. 18/054,170, mailed on Jan. 18, 2024, 8 pages.

Thiago R. S. et al., "Flexible needles detection in ultrasound images using a multi-layer perceptron network", 5th ISSNIP-IEEE Biosignals and Biorobotics Conference (2014): Biosignals and Robotics for Better and Safer Living (BRC), IEEE, May 26, 2014, pp. 1-5.

Xu, Q., Hamilton, R. J., Schowengerdt, R. A., Alexander, B., & Jiang, S. B. "Lung tumor tracking in fluoroscopic video based on optical flow." Medical physics, 35(12), 5351-5359 (Year: 2008).

Decision to Grant a Patent received for Japanese Patent Application No. 2024-017775, mailed on May 1, 2025, 5 pages (2 pages of English Translation and 3 pages of Original Document).

Office Action received for European Application No. 19822886.8, mailed on Jan. 7, 2025, 8 pages.

ULTRASOUND IMAGING SYSTEM WITH AUTOMATIC IMAGE SAVING

CROSS-REFERENCE TO RELATED APPLICATIONS

This application is a divisional of U.S. application Ser. No. 18/054,170, filed on Nov. 10, 2022, which is a continuation of U.S. application Ser. No. 16/012,627 filed on Jun. 19, 2018, now U.S. Pat. No. 11,529,116 issued on Dec. 20, 2022, which are incorporated by reference herein in their entirety.

TECHNICAL FIELD

The disclosed technology relates to ultrasound imaging systems, and in particular to systems for improving workflow within clinical settings using ultrasound imaging systems.

BACKGROUND

In ultrasound imaging, an operator of a system uses a transducer probe to obtain ultrasound images of a patient during an examination. The images captured by the system may be viewed, printed, and/or included in a patient report for diagnosis and record keeping. In addition, select images may be included in a written and/or electronic report that is used to bill the patient or their insurance for the services rendered. Depending on the examination procedure being performed, the number and subject of the images required in a report of the examination may be standardized or defined. For example, a needle injection procedure, such as an ultrasound-guided regional anesthesia injection, may require an image of the needle at a target location, an image of the needle during the injection, etc.

In a typical single operator examination, a physician or an ultrasound technician uses the imaging system to obtain all the images needed to complete the examination. However, during some needle procedures, where the care provider cannot stop mid procedure or has no free hands to control the system, a second person may assist in controlling the system settings and collecting the needed images during the procedure. The obtained images are typically stored in a buffer memory and must be reviewed after the examination is complete to mark or otherwise identify images to be used in creating a record of the examination. Often, clinicians collect a loop of images ("clip") and review the loop after the examination is complete to select images to be used in creating a record of the examination. This additional step requires extra time. If single images are collected instead of a loop, it can be difficult for the operator to know at the time of the procedure whether the required images of the examination have been captured.

DETAILED DESCRIPTION

Figure 1:
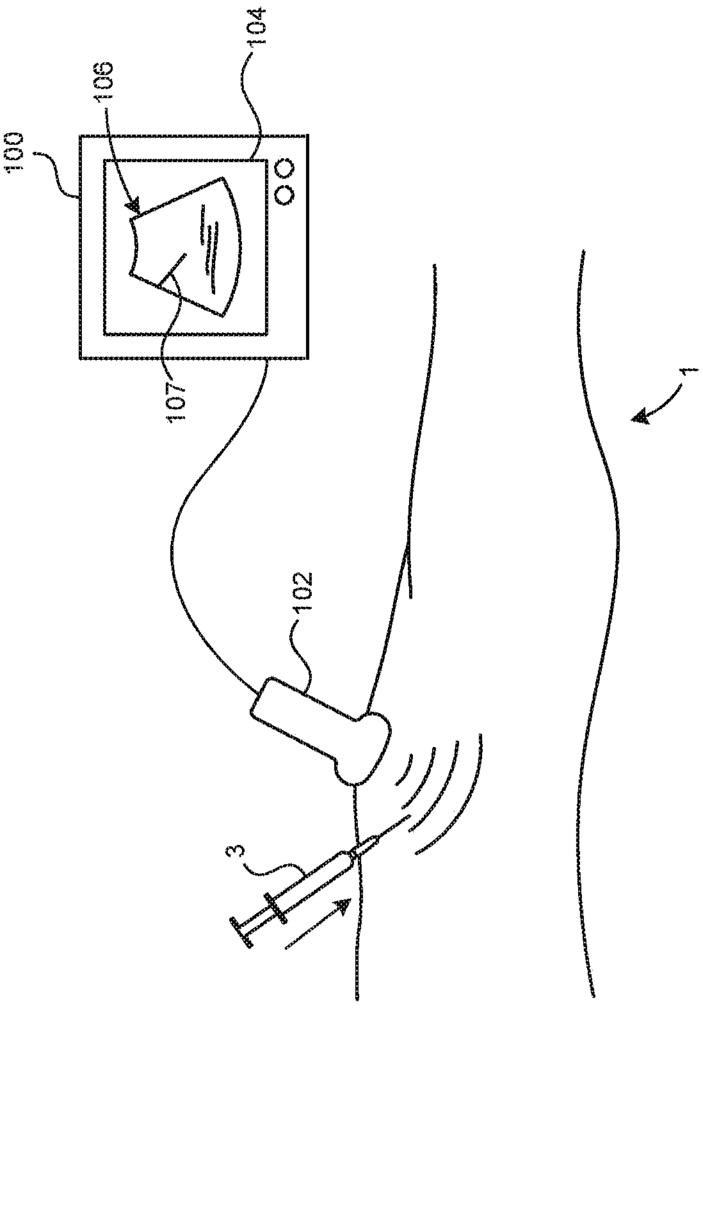
FIG. 1 is a simplified illustration of an ultrasound imaging system in accordance with an embodiment of the present technology.

Specific details of several embodiments of ultrasound systems for automatically saving ultrasound images generated during an ultrasound imaging procedure using an interventional device, and associated devices and methods, are described below reference to FIGS. 1-4. In some embodiments, for example, an ultrasound imaging system includes a transducer configured to transmit ultrasound signals to and receive ultrasound signals from a region of interest during an ultrasound-guided needle injection procedure. The ultrasound imaging system further includes receive circuitry configured to convert the received ultrasound signals into image frames of ultrasound data, and a buffer memory in which the image frames are stored. The ultrasound imaging system also includes a processor configured to analyze the image frames stored in the buffer memory and identify and mark one or more of the image frames that depict an event of the needle injection procedure—for example, the delivery of a fluid from the needle used during the procedure. In some embodiments, the processor can further be configured to save the image frames depicting the injection event in a memory—other than the buffer memory—for archival purposes.

Although many of the embodiments described below are described with respect to devices, systems, and methods for automatically saving an ultrasound image during a needle injection procedure in which a needle is used to deliver anesthesia or other drugs to a desired location, other applications and other embodiments in addition to those described herein are within the scope of the present technology. For example, at least some embodiments of the present technology may be useful for procedures employing other invasive medical instruments. It should be noted that other embodiments in addition to those disclosed herein are within the scope of the present technology.

Further, embodiments of the present technology can have different configurations, components, and/or procedures than those shown or described herein. Moreover, a person of ordinary skill in the art will understand that embodiments of the present technology can have configurations, components, and/or procedures in addition to those shown or described herein and that these and other embodiments can be without several of the configurations, components, and/or procedures shown or described herein without deviating from the present technology. The phrases "in some embodiments," "according to some embodiments," "in certain embodiments," "in the illustrated embodiment," "in other embodiments," and the like generally mean the particular feature, structure, or characteristic following the phrase is included in at least one implementation of the present technology, and may be included in more than one implementation. In addition, such phrases do not necessarily refer to the same embodiments or different embodiments.

The terminology used below is to be interpreted in its broadest reasonable manner, even though it is being used in conjunction with a detailed description of certain examples of embodiments of the technology. Indeed, certain terms may even be emphasized below; however, any terminology intended to be interpreted in any restricted manner will be overtly and specifically defined as such in this Detailed Description section.

FIG. 1 shows a representative ultrasound imaging system 100 ("system 100") that implements the present technology for imaging the tissue of a subject or patient 1. In one embodiment, the system 100 can be a hand-held, portable or cart-based system that uses a transducer probe 102 to transmit ultrasound signals into a region of interest and to receive the corresponding echo signals in order to produce an image of the tissue being scanned. The transducer probe 102 can be a one or two dimensional linear or curved transducer, a phased array transducer, or another type of ultrasound transducer as is well known in the art. The system 100 converts characteristics of the received echo signals (e.g., their amplitude, phase, power, frequency shift, etc.) into data that is quantified and displayed for the user as an image on a video monitor, screen, or other display 104 ("display 104"). As described in detail below, the images created may also be stored electronically for digital record keeping or transmitted via a wired or wireless communication link to another device or location.

In some embodiments, the system 100 can be used during a needle injection procedure in which an operator of the system 100 guides an interventional instrument such as a needle 3 into the patient 1 with one hand while holding the transducer probe 102 with the other hand. In certain embodiments, the operator can view a composite image 106 of the tissue and a representation 107 of where the needle 3 is located in the tissue. The composite image 106 can be updated on the display 104 while the needle 3 is guided to a target location within the patient 1. The target location may be a particular nerve site (e.g., when the needle injection procedure is a regional anesthesia procedure) or other area of interest such as a vessel or a particular organ (e.g., uterus, prostate, tumor, heart vessel etc.). In some embodiments, both the needle 3 and an injectate (e.g., a drug) delivered via the needle 3 can be seen in the composite image 106. For example, if the injection is made in a place with low resistance (e.g., appearing dark in the composite image 106), the injectate can fill the space such that characteristic fluid motion is visible in the composite image 106. In some embodiments, a material removed by the needle 3 (e.g., during a biopsy procedure) can be seen in the composite image 106.

Figure 2:
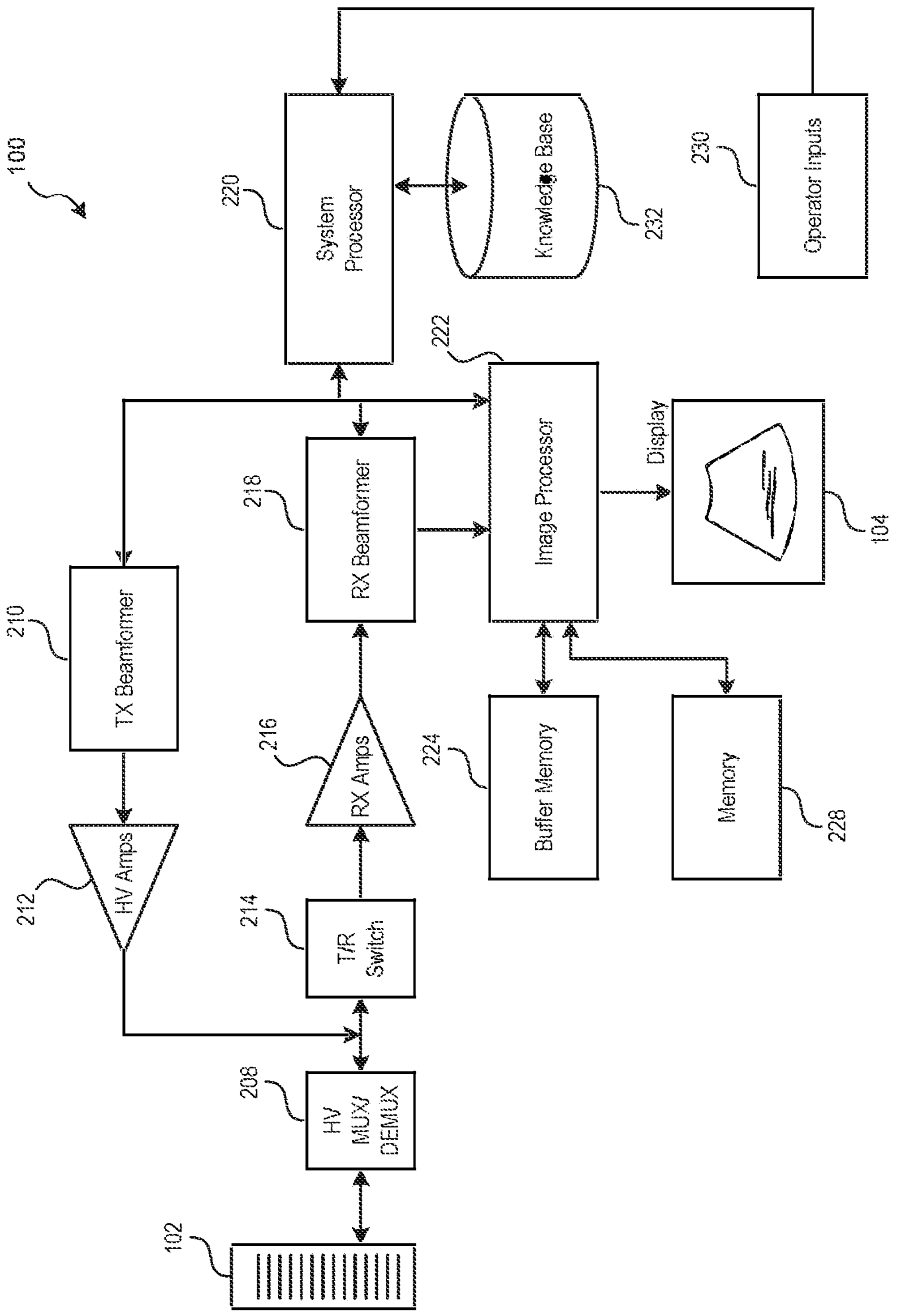
FIG. 2 is a block diagram of the ultrasound imaging system shown in FIG. 1 in accordance with an embodiment of the present technology.

FIG. 2 is a simplified block diagram of the system 100 configured in accordance with an embodiment of the present technology. As will be appreciated by those skilled in the art, the system 100 may be constructed with components that are different than those shown in FIG. 2. In addition, the system 100 can include components that are not discussed (e.g., a power supply, etc.) and that are not necessary for the understanding of how to make and use the present technology.

In the illustrated embodiment, the transducer probe 102 is connected to a high voltage multiplexer/de-multiplexer (HV mux/demux) 208 that is used select individual or groups of transducer elements in the transducer probe 102. Signals to be transmitted by the transducer probe 102 are generated by a transmit (TX) beamformer 210 that adjusts the timing of the signals in order to direct the signals in a particular direction and to focus the signals at a particular depth in the tissue. Alternatively, unfocused (plane) waves can be transmitted by the transducer probe 102. Signals from the TX beamformer 210 are amplified by one or more high-voltage amplifiers (HV amps) 212 before being applied to the HV mux/demux 208 and the transducer probe 102. In other embodiments, however, signals from the TX beamformer 210 can be passed to the transducer probe 102 directly without an intervening multiplexer/demultiplexer.

A transmit/receive (T/R) switch 214 operates to disconnect the receive electronics of the system 100 from the transducer probe 102 when the higher powered transmit pulses are being transmitted. The T/R switch 214 is closed when the system 100 is to detect the returning echo signals. Signals received by the T/R switch 214 are amplified by low-noise receive amplifiers (RX amps) 216 that implement a gain function that typically varies according to the depth from which the echo signals originate. Where the system 100 is a directional ultrasound system, the outputs of the RX amps 216 feed a receive (RX) beamformer 218 that delays and sums the amplified received echo signals. In some embodiments, the analog received signals are converted to corresponding digital signals, after amplification, with a number of analog to digital converters (not shown) that are positioned in the signal path between the RX amps 216 and the RX beamformer 218.

In some embodiments, a system processor 220, which can be implemented as one or more programmed microprocessors, is configured to execute program instructions that are stored in an internal or external computer readable memory (not shown) to control the operation of the system 100. As further illustrated in FIG. 2, beamformed ultrasound signals produced by the RX beamformer 218 are delivered to an image processor 222. The image processor 222, which may include one or more general purpose microprocessors (including the system processor 220), one or more digital signal processors (DSP), one or more graphics processor units (GPU), application-specific integrated circuits (ASIC) or the like, converts the raw, beamformed signals into a two-dimensional image frame of pixel data that can be stored in memory and shown to the operator on the display 104.

The image frames produced by the image processor 222 are stored in a buffer memory 224 (also known as a cine buffer), which in one embodiment is operated as a circular buffer of memory elements that stores a select number of image frames as they are produced during an ultrasound imaging procedure using the system 100. The image frames can be captured using either a retrospective or prospective capture mode, as is known in the art. In one embodiment, the buffer memory 224 can store 2-5 minutes of data or 3600-9000 image frames of ultrasound data or more. In one embodiment, once the buffer memory 224 is full, the oldest image frame stored in the buffer memory 224 is overwritten with a new image frame in a circular fashion. In the illustrated embodiment, a memory 228 is used to store the image frames for archival purposes. The contents of the memory 228 may be transferred to a remote patient records keeping system after an imaging procedure is complete. In some embodiments, at least some of the image frames that are stored in the memory 228 are compressed to save space and therefore may lack some detail compared with the image frames that are stored in the buffer memory 224. In some embodiments, image data other than image frames (e.g., raw image data, pre-conversion image data, etc.) can be stored in the buffer memory 224.

In the illustrated embodiment, the system 100 includes a number of operator inputs 230 such as keys, buttons, knobs, a microphone to receive voice commands, a camera to capture gestures, or software-configured controls, such as touch screen controls or the like. The operator inputs 230 allow an operator to change the operating characteristics of the system 100 and to input commands to the system processor 220.

In some embodiments, the operator begins an ultrasound imaging procedure (e.g., an examination) by using the operator inputs 230 to select a procedure type from a number of pre-defined procedure types that are shown on the display 104 or that may have a dedicated control on a keyboard or other input device of the system 100. For example, the imaging procedure could be a regional anesthesia injection or other ultrasound-guided needle injection procedure. Each procedure type may be associated with particular views and/or measurements that are to be captured by the operator during the specific procedure. For example, some needle injection procedures may require an image of the needle at the target region with the patient, an image of the needle during injection of a drug or other injectate, etc. For example, a nerve block procedure may require that three or more different image frames be recorded including views of (i) a needle approaching a target nerve, (ii) the needle at the position of the target nerve, and (iii) anesthetic being delivered around the target nerve. Such views may be required to be stored (e.g., archived) by the medical facility or operator for insurance billing purposes. In the illustrated embodiment, the views and/or measurements required by the various procedure types are stored in a knowledge base 232 (e.g., a memory, database, etc.) that is accessible to the system processor 220. In some embodiments, the knowledge base 232 can further store one or more parameters, image frames, or other data from previous examinations that can be, for example, compared to the image frames stored in the buffer memory 224 as described in detail below.

After selecting a particular imaging procedure, the operator can use one or more of the operator inputs 230 (e.g., an on-screen button, footswitch, control on an imaging probe, etc.) to begin capturing ultrasound image frames using the system 100. These image frames are produced and stored in the buffer memory 224 until the operator uses one or more of the operator inputs 230 to halt the image capture process. In some embodiments, the image capture process can be halted based on other criteria such as, for example, a timer, an electrocardiogram signal, etc. As will be appreciated, the buffer memory 224 can be constructed to store several thousand image frames of ultrasound data.

In the past, using conventional ultrasound systems, the operator was required to take the time to review/search through all of the stored image frames to select which frames would be included in a patient's record and/or submitted for billing purposes. Moreover, the review/search for relevant images was conducted after the imaging procedure concluded—meaning it was not possible for the operator to know with certainty during a needle injection procedure whether they captured the required views (e.g., for billing purposes). In some other conventional ultrasound systems, the operator could press a button on an ultrasound probe or use a voice control during a procedure to print or save particular images—for example, those taken at approximately the time of an injection. While such systems may reduce the amount of review required by the operator to identify relevant image frames, buttons may be pressed accidentally, and voice controls may be accidentally activated in noisy environments. Furthermore, it is often cumbersome for the operator to conduct a needle injection procedure while simultaneously triggering an ultrasound system to save certain images during the procedure.

In contrast to conventional systems, the system 100 of the present technology is configured to automatically identify (e.g., select, determine, etc.) and save image frames that are relevant to, or required, by a needle injection procedure—for example, those image frames depicting a particular event, trigger, or aspect of the needle injection procedure (referred to herein as an "injection event"). For example, the system 100 can be configured to automatically identify image frames that depict a specified injection event such as a needle being positioned at or approaching a target location, an injection taking place, etc. Specifically, the system processor 220, the image processor 222, and/or another suitable processor such as a DSP or a GPU can execute a number of programmed instructions to analyze the image frames that are stored in the buffer memory 224 and identify one or more of the image frames that likely depict the specified injection event. In other embodiments, image data other than image frames (e.g., pre-conversion image data) can be analyzed to identify portions of the image data that depict or relate to the specified injection event.

The identified image frames can be saved to the memory 228 for archival or other purposes. In some embodiments, the identified image frames are stored in the memory 228 with lossless compression or with little or no compression compared to the unselected image frames generated during the examination in order to retain more image detail. In certain embodiments, the identified image frames are marked for inclusion in, or automatically entered into, a patient report of an examination. In some embodiments, the system 100 can generate an indication (e.g., a sound, display, etc.) to provide real-time or near-real-time feedback to the operator that image frames showing the specified injection event were successfully captured.

Figure 3:
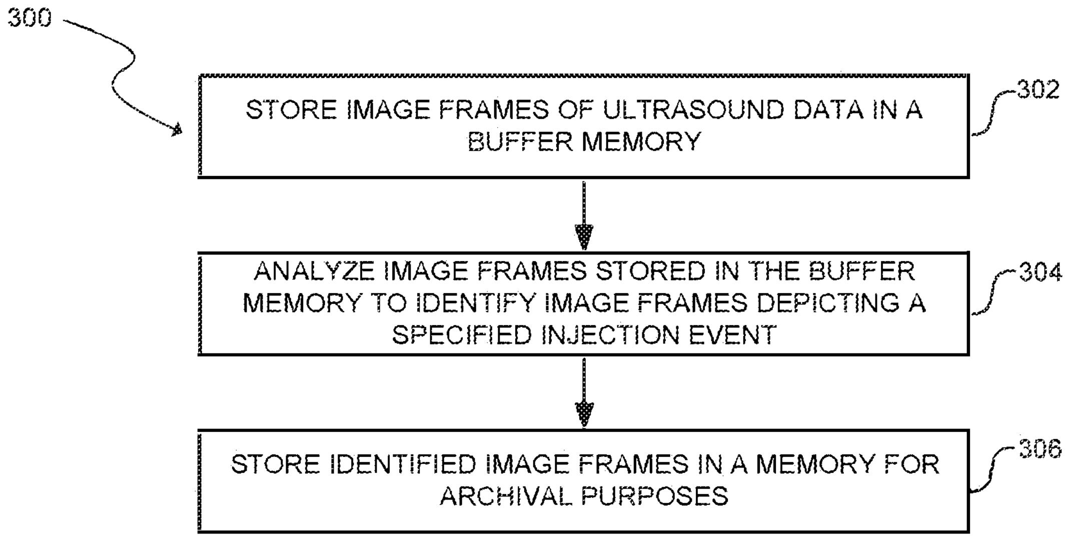
FIG. 3 is a flow diagram of a method or process of identifying image frames stored in a buffer memory that depict an injection event in accordance with an embodiment of the present technology.

The system processor 220 (or another processor) can automatically identify image frames stored in the buffer memory 224 that likely depict a specified injection event in a number of different manners. FIG. 3, for example, is a flow diagram of a process or method 300 performed by one or more of the processors in the system 100 for identifying image frames that depict an injection event using frame-to-frame comparison in accordance with embodiments of the present technology. Beginning at block 302, the method 300 includes generating ultrasound signals and receiving the corresponding echo signals for a needle injection procedure and storing image frames of ultrasound data about the procedure in the buffer memory 224, as described in detail above. At block 304, the method includes comparing and/or analyzing image frames stored in the buffer memory 224 to identify the image frames that depict the specified injection event. In some embodiments, for example, the system processor 220 correlates and/or compares the image frames stored in the buffer memory 224 to detect changes between the image frames such as those caused by motion of a needle and/or the fluid injected from the needle.

For example, the system processor 220 can use well-known image processing methods to estimate and characterize the point correspondence from one image frame to the next in the vicinity of the needle. For example, the system processor 220 can estimate the correspondence (or motion) of each point of interest by maximizing a figure of merit for the match between a patch of one image frame centered about the point in question with a sliding window in the next image frame for each image frame stored in the buffer memory 224. That is, the system processor 220 can estimate flow vectors for each or a subset of pixels between two or more image frames. Potential figures of merit include 2D correlation, mutual information, or structural similarity. In some embodiments, regularization or pre-processing may be applied to assist in (e.g., lower the processing costs of) estimating the correspondence of each point of interest. In other embodiments, optical flow methods such as the Lucas Kanade or Horn-Schunck may be employed to establish the point correspondences (e.g., flow vectors). In either case, the flow vector properties can be classified to indicate the needle and/or injectate.

Regardless of the specific image processing method(s) employed, the system processor 220 can identify that certain image frames stored in the buffer memory 224 likely depict the specified injection event based on the estimated optical flow/motion between the image frames. In some embodiments, for example, the system processor 220 can determine that the needle is stationary or generally stationary in certain image frames and thus that the needle is positioned at the target location and/or that an injection is occurring in those image frames. Similarly, a detection of fluid motion around the needle tip in certain image frames can indicate that the injection is depicted in those frames.

In other embodiments, the system processor 220 may execute instructions that implement a trained neural network or a machine learning algorithm to analyze/compare image frames stored in the buffer memory 224 in order to identify the image frames that depict the specified injection event. The machine learning algorithm can be an artificial neural network or deep learning algorithm that is trained to recognize motion indicative of the injection event in the image frames (e.g., the swirl or expansion of the fluid of the injection around the tip of the needle). In some embodiments, for example, a neural network can be used to detect the injection event based on the differences between image frames in the buffer memory 224 (e.g., based on a time series of image frames). In some embodiments, the machine learning algorithm can be trained based one or more image frames that were generated and saved in one or more previous examinations and that are similar to the image frames required to be saved in the current examination. These previous images can be stored in, for example, the knowledge base 232. Based on the previous images, the machine learning algorithm can determine the image frames in the buffer memory 224 that, for example, bear the closest resemblance to the previous images and thus likely depict the injection event. In this manner, the system processor 220 can identify the image frames that likely depict the injection event based on the historical data/examples from previous examinations.

In certain embodiments, the system processor 220 can further mark or identify a particular region (e.g., a sub-region) in one or more of the image frames that likely depicts the injection. For example, the system processor 220 could automatically determine a bounding box around the likely region of injection based on classification of flow vectors calculated or determined for the image frame(s).

In some embodiments, the system processor 220 can be configured to analyze only a portion (e.g., a specific region) of the image frames and/or a subset of the total number of image frames in order to detect the specified injection event. For example, the system processor 220 can be configured analyze only a portion (e.g., a region) of the image frames that is proximate to a determined location of the needle. Likewise, the system processor 220 could employ different levels or types of imaging processing methods on different subsets of the image frames stored in the buffer memory 224. For example, the system processor could analyze the image frames stored in the buffer memory 224 until detecting that the needle has stopped moving, and then analyze subsequently generated/stored image frames to detect those image frames that depict the fluid from the injection around the needle. Such embodiments can advantageously reduce the processing burden of the system 100 by localizing some of the imaging processing steps to a subset of the image frames stored in the buffer memory 224.

At bock 306, the method 300 includes automatically storing the image frames identified as depicting the injection event in a memory for archival purposes (e.g., for inclusion in a patient report, billing record, or other report). For example, the image frames can be stored in the memory 228 and/or in a different memory accessible to the system processor 220. In some embodiments, the identified image frames can be marked or flagged in the buffer memory 224 in addition to or instead of being stored in a memory for archival purposes.

Figure 4:
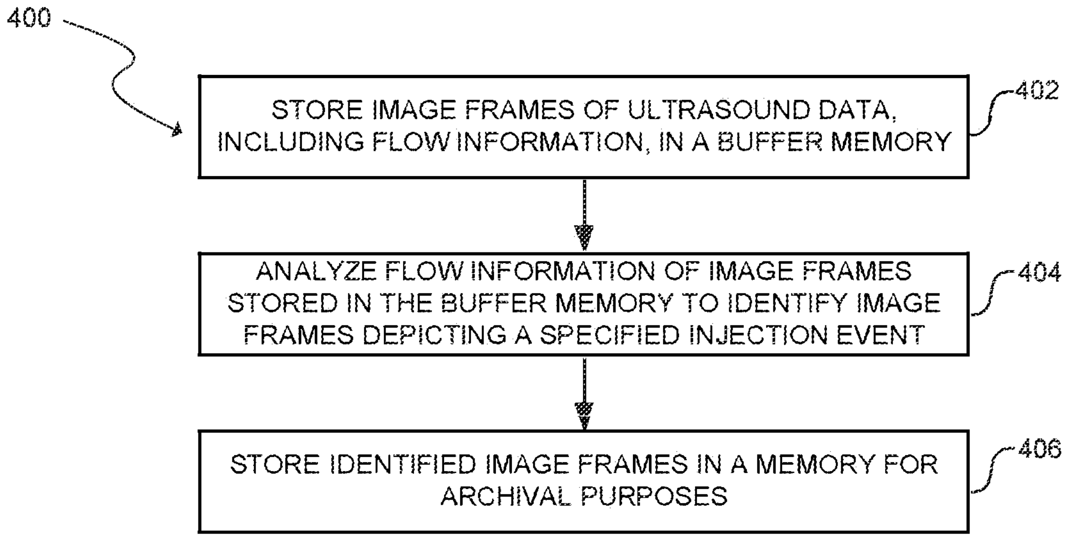
FIG. 4 is a flow diagram of a method or process of identifying image frames stored in a buffer memory that depict an injection event in accordance with another embodiment of the present technology.

In some embodiments, the system processor 220 can automatically identify image frames stored in the buffer memory 224 in other manners (e.g., other than by a frame-to-frame comparison). FIG. 4, for example, is a flow diagram of a process or method 400 performed by one or more of the processors in the system 100 for identifying image frames that depict an injection event based on flow information in the image frames, in accordance with embodiments of the present technology. Beginning at block 402, the method 400 includes generating ultrasound signals and receiving the corresponding echo signals for a needle injection procedure and storing image frames of ultrasound data about the procedure in the buffer memory 224, as described in detail above. More specifically, in some embodiments, the system 100 can be operated in a Doppler Mode or another color flow imaging mode that generally correlates multiple ultrasound signal pulses into a single image frame that contains motion or flow information (often displayed in color), as is known in the art. In some embodiments, the color flow imaging need not employ the entire color flow processing chain-instead segmentation and classification of a subset of the signals (e.g., lag-0 correlations, lag-1 correlations, etc.) can be used to produce the flow information. At block 404, the system processor 220 can proceed to analyze the flow information of the image frames stored in the buffer memory 224 to identify those image frames depicting the specified injection event.

In some embodiments, the method 400 requires a relatively greater amount of front-end processing by the processor(s) than the method 300 illustrated in FIG. 3, because multiple ultrasound signals pulses are used to generate each image frame. Accordingly, the frame rate of the system 100 can be slower when performing the method 400 as compared to the method 300. In certain embodiments, to improve the frame rate of the system 100 while performing the method 400, the system 100 can be configured to capture flow information (e.g., to generate, detect, and correlate multiple ultrasound signal pulses) for only a portion or region of each image frame. In some embodiments, for example, the system 100 can determine a bounding box (e.g., a virtual color box) or other region in which to search for the specified injection event that is smaller than the entire image frame. For example, the system processor 220 can execute instructions that implement an image classification algorithm (e.g., a detection, trained neural network, or machine learning algorithm) to detect the location of the needle (e.g., by detecting a bright reflector, either stationary or moving) and/or the location of the needle tip (e.g., by detecting a transition from a bright reflector). The system processor 220 can then specify a small region around the needle in which to search for an injection of fluid from the needle by generating flow information for the small region. In some embodiments, the detected location of the needle in one image frame can be used to expedite the search for the needle in another image frame (e.g., a subsequent image frame). That is, once the needle is detected in one image frame, the entirety of each subsequent image frame does not need to be classified from there forward in time. Finally, at block 406, the method 400 includes automatically storing the image frames identified as depicting the injection event in a memory for archival purposes, or otherwise marking or flagging the image frames in the buffer memory 224.

In general, the system 100 can automatically identify image frames stored in the buffer memory 224 that likely depict the specified injection event using any of frame-to-frame image processing, image processing using trained neural networks or machine learning algorithms, optical flow (e.g., classification of flow vectors that indicate the cessation of movement of a needle structure and/or the swirling or expanding of a flow pattern of injectate), color flow imaging, or combinations thereof. For example, simple frame-to-frame comparison methods could be used to detect motion of the needle between image frames, and specifically to detect that motion of the needle has stopped. A trained neural network or machine learning algorithm could then be employed to detect the needle tip in subsequently generated image frames. Finally, a region around the identified needle tip could be interrogated using color flow imaging to detect the injection of fluid from the needle tip. In this manner, the system 100 can automatically accurately identify image frames depicting the specified injection event while reducing the processing requirements of the system 100 compared to, for example, generating flow information for each full image frame produced during a procedure.

In some embodiments, the system 100 is configured to analyze the image frames stored in the buffer memory 224 in real-time or near-real-time as they are generated and added to the buffer memory 224. In such embodiments, after identifying that one or more of the image frames depicts the specified injection event, the system 100 can be configured to generate a notification or indication that at least one of the image frames depicts the injection event. In some embodiments, for example, the system processor 220 can cause a notification to be displayed on the display 104 or a sound to be played via a speaker of the system 100. Accordingly, the system 100 can advantageously provide feedback alerting the operator of the system 100—during the examination—that the necessary image frames were captured. In other embodiments, image frames from an entire ultrasound procedure can be accessed and analyzed after the procedure is concluded to automatically determine and save image frames depicting the specified injection event.

In some embodiments, the image frames are associated with meta-data (e.g., narrative information) about the image frame. The meta-data may include the type of tissue being imaged and one or more parameters of the system 100 used to obtain the image. Such parameters can include the operating mode of the ultrasound machine (B-mode, Doppler Mode, Power mode, etc.) as well as power settings, pulse repetition rate, focal depth, probe used, likelihood of needle presence/motion, etc. In some embodiments, the system processor 220 can insert one or more of the identified image frames into a patient record (e.g., PACS system, knowledge repository, etc.), patient chart, or other record, while also inserting (e.g., pre-populating) the corresponding operating parameters of the ultrasound machine that were used to obtain the image frame and/or other meta-data so that the operator does not have to enter them manually.

Embodiments of the subject matter and the operations described in this specification can be implemented in digital electronic circuitry, or in computer software, firmware, or hardware, including the structures disclosed in this specification and their structural equivalents, or in combinations of one or more of them. Embodiments of the subject matter described in this specification can be implemented as one or more computer programs, i.e., one or more modules of computer program instructions, encoded on computer storage medium for execution by, or to control the operation of, data processing apparatus.

A computer storage medium can be, or can be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially-generated propagated signal. The computer storage medium also can be, or can be included in, one or more separate physical components or media (e.g., multiple CDs, disks, or other storage devices). The operations described in this specification can be implemented as operations performed by a data processing apparatus on data stored on one or more computer-readable storage devices or received from other sources.

The term "processor" encompasses all kinds of apparatus, devices, and machines for processing data, including by way of example a programmable processor, a computer, a system on a chip, or multiple ones, or combinations, of the foregoing. The apparatus can include special purpose logic circuitry, e.g., an FPGA (field programmable gate array) or an ASIC (application-specific integrated circuit). The apparatus also can include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub-programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform actions by operating on input data and generating output. The processes and logic flows can also be performed by, and apparatus can also be implemented as, special purpose logic circuitry, e.g., an FPGA (field programmable gate array) or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only memory or a random access memory or both. The essential elements of a computer are a processor for performing actions in accordance with instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. Devices suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in, special purpose logic circuitry.

To provide for interaction with a user, embodiments of the subject matter described in this specification can be implemented on a imaging system having a display device, e.g., an LCD (liquid crystal display), LED (light emitting diode), or OLED (organic light emitting diode) monitor, for displaying information to the operator and a keyboard and a pointing device, e.g., a mouse or a trackball, by which the operator can provide input to the computer. In some implementations, a touch screen can be used to display information and to receive input from a user. Other kinds of devices can be used to provide for interaction with an operator as well; for example, feedback provided to the operator can be any form of sensory feedback, e.g., visual feedback, auditory feedback, or tactile feedback; and input from the operator can be received in any form, including acoustic, speech, or tactile input. In addition, a computer can interact with an operator by sending documents to and receiving documents from a device that is used by the user; for example, by sending web pages to a web browser on a user's client device in response to requests received from the web browser.

From the foregoing, it will be appreciated that specific embodiments of the technology have been described herein for purposes of illustration, but that various modifications may be made without deviating from the disclosure. Accordingly, the invention is not limited except as by the appended claims. Furthermore, certain aspects of the new technology described in the context of particular embodiments may also be combined or eliminated in other embodiments. Moreover, although advantages associated with certain embodiments of the new technology have been described in the context of those embodiments, other embodiments may also exhibit such advantages and not all embodiments need necessarily exhibit such advantages to fall within the scope of the technology. Accordingly, the disclosure and associated technology can encompass other embodiments not expressly shown or described herein.

The invention claimed is:

1. A method performed by a processor in an ultrasound system, the method comprising:

receiving ultrasound signals from a region of interest during a needle injection procedure;

converting the ultrasound signals into image frames of ultrasound data;

storing the image frames in a buffer memory;

obtaining a first subset of the image frames from the buffer memory;

identifying, from the first subset, a first image frame indicating that a needle has approached to a target location within a region of interest using a first image processing technique that is an image frames comparing technique;

obtaining a second subset of the image frames from the buffer memory, wherein the second subset of the image frames have been generated and stored subsequent to the first subset in the buffer memory;

identifying, from the second subset, a second image frame indicating a tip of the needle using a second image processing technique that is a machine learning algorithm image processing technique; obtain a third subset of the image frames from the buffer memory, wherein the third subset of the image frames have been generated and stored subsequent to the second subset in the buffer memory; identify, from the third subset, a third image frame indicating an injection of fluid from the tip of the needle taking place within the region of interest using a third image processing technique that is an optical flow imaging technique to reduce processing burden for the system.

2. The method of claim 1, further comprising:

saving at least one of the first image frame, the second image frame, and the third image frame into a first memory.

3. The method of claim 1, wherein the image frames are associated with meta-data indicating one or more of a tissue type, a system operating mode, a power setting, pulse repetition rate, a focal depth, a probe used, a likelihood of the needle presence, and a likelihood of the needle motion.

4. The method of claim 1, wherein at least one of the first image frame, the second image frame, and the third image frame is identified based on historical data from a previous examination.

5. The method of claim 2, wherein at least one of first image frame, the second image frame, and the third image frame is stored in the first memory with the meta-data.

6. The method of claim 1, further comprising marking, in the buffer memory, at least one of the first image frame, the second image frame and the third image frame for inclusion into a patient record.

7. The method of claim 1 further comprising:

comparing the first subset of the image frames to each other to detect a motion, wherein the motion is associated with at least one of the needle, a fluid delivered by the needle, or a material removed by the needle, and wherein the first image frame is identified based on the comparing.

8. The method of claim 1, further comprising:

identifying, from the third subset, a fourth image frame indicating the cessation of movement of the needle at the target location within the region of interest using the optical flow imaging technique.

9. The method of claim 1, further comprising:

generating an indication to an operator that the first image frame depicts the first injection event that the needle has approached to the target location within the region of interest.

10. The method of claim 1, further comprising:

displaying the image frames on a display device.

11. The method of claim 1, further comprising:

transmitting, in two or more pulses, the ultrasound signals to the region of interest during the needle injection procedure.

12. The method of claim 1, further comprising:

marking a region of at least one of the first subset of image frames that likely depicts that the needle has approached to the target location within the region of interest.

13. A non-transitory machine readable medium comprising instructions that cause a data processing system to perform operations comprising:

receiving ultrasound signals from a region of interest during a needle injection procedure;

converting the ultrasound signals into image frames of ultrasound data;

storing the image frames in a buffer memory;

obtaining a first subset of the image frames from the buffer memory;

identifying, from the first subset, a first image frame indicating that a needle has approached to a target location within a region of interest using a first image processing technique that is an image frames comparing technique;

obtaining a second subset of the image frames from the buffer memory, wherein the second subset of the image frames have been generated and stored subsequent to the first subset in the buffer memory;

identifying, from the second subset, a second image frame indicating a tip of the needle using a second image processing technique that is a machine learning algorithm image processing technique; obtain a third subset of the image frames from the buffer memory, wherein the third subset of the image frames have been generated and stored subsequent to the second subset in the buffer memory; identify, from the third subset, a third image frame indicating an injection of fluid from the tip of the needle taking place within the region of interest using a third image processing technique that is an optical flow imaging technique to reduce processing burden for the system.

14. The non-transitory machine readable medium of claim 13, further comprising instructions that cause the data processing system to perform operations comprising saving at least one of the first image frame, the second image frame, and the third image frame into a first memory.

15. The non-transitory machine readable medium of claim 13, wherein the image frames are associated with meta-data indicating one or more of a tissue type, a system operating mode, a power setting, pulse repetition rate, a focal depth, a probe used, a likelihood of the needle presence, and a likelihood of the needle motion.

16. The non-transitory machine readable medium of claim 13, wherein at least one of the first image frame, the second image frame, and the third image frame is identified based on historical data from a previous examination.

17. The non-transitory machine readable medium of claim 13, wherein at least one of first image frame, the second image frame, and the third image frame is stored in the first memory with the meta-data.

18. The non-transitory machine readable medium of claim 13, further comprising instructions that cause the data processing system to perform operations comprising marking, in the buffer memory, at least one of the first image frame, the second image frame and the third image frame for inclusion into a patient record.

19. The non-transitory machine readable medium of claim 13, further comprising instructions that cause the data processing system to perform operations comprising identifying, from the third subset, a fourth image frame indicating the cessation of movement of the needle at the target location within the region of interest using the optical flow imaging technique.

20. The non-transitory machine readable medium of claim 13, further comprising instructions that cause the data processing system to perform operations comprising comparing the first subset of the image frames to each other to detect a motion, wherein the motion is associated with at least one of the needle, a fluid delivered by the needle, or a material removed by the needle, and wherein the first image frame is identified based on the comparing.

* * * * *